United States Patent
Nieendick et al.

(10) Patent No.: US 12,201,711 B2
(45) Date of Patent: Jan. 21, 2025

(54) WAX DISPERSIONS HAVING CONDITIONING PROPERTIES

(71) Applicant: BASF SE, Ludwigshafen (DE)

(72) Inventors: Claus Nieendick, Düsseldorf-Holthausen (DE); Werner Mauer, Düsseldorf-Holthausen (DE); Anke Becker, Düsseldorf-Holthausen (DE); Sybille Cornelsen, Monheim (DE)

(73) Assignee: BASF SE (DE)

( * ) Notice: Subject to any disclaimer, the term of this patent is extended or adjusted under 35 U.S.C. 154(b) by 893 days.

(21) Appl. No.: 17/057,755

(22) PCT Filed: May 27, 2019

(86) PCT No.: PCT/EP2019/063639
§ 371 (c)(1),
(2) Date: Nov. 23, 2020

(87) PCT Pub. No.: WO2019/228975
PCT Pub. Date: Dec. 5, 2019

(65) Prior Publication Data
US 2023/0240956 A1    Aug. 3, 2023

(30) Foreign Application Priority Data
May 30, 2018 (EP) .................................... 18174997

(51) Int. Cl.
| A61K 8/37 | (2006.01) |
| A61K 8/04 | (2006.01) |
| A61K 8/44 | (2006.01) |
| A61K 8/46 | (2006.01) |
| A61Q 5/12 | (2006.01) |

(52) U.S. Cl.
CPC ............... *A61K 8/375* (2013.01); *A61K 8/04* (2013.01); *A61K 8/44* (2013.01); *A61K 8/463* (2013.01); *A61Q 5/12* (2013.01)

(58) Field of Classification Search
CPC . A61K 8/375; A61K 8/04; A61K 8/44; A61K 8/463; A61Q 5/12
See application file for complete search history.

(56) References Cited

U.S. PATENT DOCUMENTS

| 5,888,487 A * | 3/1999 | Baumoeller ............. A61Q 5/02 424/501 |
| 10,383,801 B2 | 8/2019 | Rose et al. |
| 2004/0247630 A1 | 12/2004 | Seipel et al. |

FOREIGN PATENT DOCUMENTS

| BR | PI0810776 B1 * | 7/2016 |
| CN | 1323196 A | 11/2001 |
| DE | 4232506 A1 | 3/1994 |
| DE | 19511572 C2 | 2/1998 |
| DE | 10150725 A1 | 4/2003 |
| FR | 2252840 A1 | 6/1975 |
| GB | 1494915 A | 12/1977 |
| JP | 2005-505601 A | 2/2005 |
| JP | 2016-530306 A | 9/2016 |
| WO | WO-02/05781 A1 | 1/2002 |
| WO | WO-03/033634 A1 | 4/2003 |
| WO | WO-2014/046252 A1 | 3/2014 |

OTHER PUBLICATIONS

BR PI0810776B1 translation (Year: 2016).*
European Search Report for EP Patent Application No. 18174997.9, Issued on Dec. 11, 2018, 3 pages.
"Dove Pro Age Shampoo", Cosmetic-Info.jp [Online], Unilever Japan, Aug. 27, 2007, 1 page. URL—https://www.cosmetic-info.jp/.
"Natur Vital Non-Silicon A Shampoo", Cosmetic-Info.jp [Online], Ishizawa Laboratories, Jul. 5, 2010, 2 pages.
International Application No. PCT/EP2019/063639, International Search Report, mailed Aug. 16, 2019.

* cited by examiner

*Primary Examiner* — Snigdha Maewall
(74) *Attorney, Agent, or Firm* — Faegre Drinker Biddle & Reath LLP

(57) ABSTRACT

What are described are aqueous wax dispersions based on ethylene glycol fatty acid esters of specific fatty acids that can be used both as opacifiers and for improvement of conditioning action in formulations for haircare.

18 Claims, No Drawings

WAX DISPERSIONS HAVING CONDITIONING PROPERTIES

CROSS-REFERENCE TO RELATED APPLICATIONS

This is the U.S. national phase of International Application No. PCT/EP2019/063639, filed May 27, 2019, which claims the benefit of European Patent Application No. 18174997.9, filed May 30, 2018.

FIELD OF THE INVENTION

The invention relates to cloudy wax dispersions comprising selected ethylene glycol fatty acid esters as wax bodies, fatty acid partial glycerides and anionic and amphoteric surfactants that have conditioning properties, and to the use of such wax dispersions as the opacifiers and/or conditioners and as boosters of cationically modified guar derivatives.

PRIOR ART

Cosmetic formulations for the skin and hair, such as hair shampoos, hair conditioners or liquid hand soap, are also commonly formulated differently in terms of their visual appearance. What are usually desired are products having a mica or pearlescent effect, or products that have a white cloudy appearance but are not shiny and are usually described as "milky". The effect of white cloudiness is usually achieved by adding what are called "opacifiers". For a homogeneous appearance, one feature that opacifiers must have is that of being finely divided. Furthermore, they must be homogeneously distributable in the cosmetic formulations and must not lose cloudiness or even separate in the course of storage.

Typical opacifiers are dispersions of finely divided polymers or solids that comprise essentially only a wax body and a suitable emulsifier, in addition to water and/or a polyol such as glycerol. The opacifiers known from the prior art are often based on copolymers of acrylic or methacrylic acid and styrene as wax body, and are non-biodegradable.

German patent DE 19511572 C discloses opacifier concentrates based on wax bodies, sugar surfactants and partial glycerides that have good biodegradabilities, but are in need of improvement with regard to fine division.

International patent application WO 03/033634 discloses low-viscosity opacifiers comprising fatty acid polyglycol esters, amphoteric surfactants and also fatty acid polyglycerides, and optionally polyols, in particular limited weight ratios. The advantageous properties such as fine division, good flow and pumping properties, low-viscosity, good storage stability and pleasing white cloudiness can be obtained according to this international application only when no anionic surfactants are present. In the presence of anionic surfactants, what are obtained are not opacifiers but pearlescent agents, and an unacceptable rise in viscosity is generated.

Accordingly, it was an object of the present invention to provide wax dispersions based on wax bodies which, even in the presence of anionic surfactants, especially of fatty alcohol (ether) sulfates, show white cloudiness and no pearlescence.

Furthermore, the wax dispersions were additionally to have a conditioning effect such as improved wet and dry combability in hair shampoos, or a pleasant, soft physical feel for haircare products, even in the presence of widely used anionic surfactants.

A further aim was to provide storage-stable wax dispersions that show unchanged white cloudiness in uniform quality over a long period and have very good homogeneity and a distinct reduction in average particle size (fine division) compared to the prior art.

DESCRIPTION OF THE INVENTION

The invention provides aqueous wax dispersions suitable as opacifier and/or conditioner for cosmetic formulations, comprising
(a) ethylene glycol fatty acid esters as wax body and
(b) fatty acid partial glycerides and
(c) anionic surfactants selected from the group formed by fatty alcohol (ether) sulfates and
(d) amphoteric surfactants selected from the group formed by betaines,
wherein the ethylene glycol fatty acid esters (a) are formed by stearic acid or a mixture of fatty acids comprising 85-100% by weight—based on fatty acid—of stearic acid.

In the context of the present invention, "conditioners" are compositions in the field of cosmetic formulations that show a conditioning effect when applied to the hair and/or skin.

In the context of the present invention, compositions have a conditioning effect on the skin when they give rise to a positive skinfeel after direct contact with the human skin, which is assessed positively by testers in practice, such as in panel tests with sensory impressions in relation to particular parameters such as "dryness of the skin", "softness of the skin".

In the context of the present invention, the compositions have a conditioning effect on hair when it shows improved combability after treatment thereof. Better combability can occur in the wet and/or dry state, both over the length and in the tips (called disentanglability) of the hair. Conditioning compositions also improve tactile properties of the hair, such as smoothness, softness, suppleness, hair shine, lower electrostatic charge and better shapability.

Opacifiers, which are also referred to as whiteners, in the context of the present invention are agents that give rise to white cloudiness without pearlescence.

In the context of the present invention, median particle size (d50) and particle size distribution in μm were determined by means of laser diffraction with the Mastersizer® 2000 instrument and the corresponding product description from MALVERN INSTRUMENTS GmbH, Marie-Curie-Straße 4/1, 71083 Herrenberg, Germany.

The wax dispersions of the invention comprise, as wax body a), specific ethylene glycol fatty acid esters. Ethylene glycol fatty acid esters follow the general formula

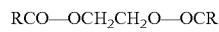

RCO—OCH$_2$CH$_2$O—OCR and are preparable by esterification of ethylene glycol with fatty acids or fatty acid mixtures. Ethylene glycol fatty acid esters, known by the INCI name ethylene glycol distearate, have technically different esterification levels and fatty acid cuts. According to the present invention, the fatty acid mixture comprises 85% to 100% by weight of stearic acid and hence much higher proportions of stearic acid than the about 50% by weight in commercial technical grade mixtures that are sold by way of example under the Cutina® AGS name by BASF Personal Care Nutrition GmbH.

The fatty acid mixture in the context of the invention preferably comprises 85% to 100% by weight of stearic acid and 0% to 15% by weight of other fatty acids having 12 to 22 carbon atoms-based on the total amount of fatty acid. The fatty acid mixture preferably comprises 90% to 98% by weight of stearic acid and 2% to 10% by weight of other saturated fatty acids having 16 to 22 carbon atoms-based on the total amount of stearic acid, and the fatty acid mixture especially consists of 90% to 96% by weight of stearic acid and 4% to 10% by weight of other saturated fatty acids having 16 to 22 carbon atoms. Other saturated fatty acids having 16 to 22 carbon atoms are palmitic acid, arachic acid and behenic acid.

Ethylene glycol fatty acid esters that are preferred in the context of the invention are ethylene glycol fatty acid diesters which, for technical reasons, comprise 90% to 100% ethylene glycol diesters and 0% to 10% by weight ethylene glycol fatty acid monoesters.

Such ethylene glycol fatty acid esters having a preferred ethylene glycol di-fatty acid content and stearic acid content in the fatty acid mixture are available on the market under the Cutina® KE2747 brand name, BASF.

Within the wax body a), very particularly suitable ethylene glycol fatty acid esters are those that have a melting point in the range from 72 to 80° C.

For the wax dispersions of the invention, it is advisable that the wax bodies a) are present in amounts of 20% to 35%, preferably 25% to 30%, by weight-based on the wax dispersion.

Preferably, in the wax dispersions of the invention, a) has an average particle diameter in the range from 1 to 4 μm. Preferably, the distribution of the particle diameters is such that more than 50% is below 3 μm and 90% of all particles below 7 μm.

Especially suitable are wax bodies a) that show a predominantly spherical particle shape, with 70% of all particles having a three-dimensional structure very particularly characterized by a ratio of height:width:length of 1:1:1. Such particle shapes and particle amounts are determinable by means of laser diffraction with the Mastersizer® 2000 instrument and the corresponding product description from MALVERN INSTRUMENTS GmbH, Marie-Curie-Straße 4/1, 71083 Herrenberg, Germany.

As further component b), the wax dispersions comprise fatty acid partial glycerides. Fatty acid partial glycerides in the context of the invention are monoglycerides, diglycerides and technical grade mixtures thereof, which, as a result of preparation, may also comprise small amounts of glycerol and triglycerides. Preferred technical grade mixtures of fatty acid partial glycerides b) are those that have a monoglyceride content in the range from 50% to 95% by weight, preferably 60% to 90%, by weight, and are also referred to hereinafter as glycerol fatty acid monoesters.

In the context of the present invention, preference is given to fatty acid partial glycerides (b) selected from the group formed by glycerol fatty acid monoesters, wherein suitable fatty acids are lauric acid, isotridecanoic acid, myristic acid, palmitic acid, palm oleic acid, stearic acid, isostearic acid, oleic acid, elaidic acid, petroselic acid, linoleic acid, linolenic acid, eleostearic acid, arachic acid, gadoleic acid, behenic acid and erucic acid, and technical grade mixtures thereof. Particular preference is given to glycerol fatty acid monoesters wherein the fatty acids have 12 to 18 carbon atoms, preference being given to (b) a glycerol fatty acid monoester of a fatty acid mixture comprising 90% to 100% by weight of oleic acid-based on fatty acid mixture.

An example of a suitable technical grade product on the market is Monomuls® 90-O 18, a commercial product from BASF Personal Care & Nutrition GmbH.

The fatty acid partial glycerides b) are present in amounts of 0.5% to 3.0%, preferably 1.0% to 2%, by weight-based on the aqueous dispersion.

Aqueous wax dispersions comprising glycerol monooleate, which is particularly preferred, show low viscosities, which is advantageous for processing, pumpability.

With regard to cloudiness and conditioning properties, it is advantageous when the aqueous dispersions a) and b) are present in the dispersion in a weight ratio of a):b) in the range from 15:1 to 20:1, preferably 17:1 to 18.5:1.

Constituents c) present in the wax dispersions are anionic surfactants, these being selected from the group formed by fatty alcohol (ether) sulfates.

Preference is given especially to fatty alcohol (ether) sulfates of the general formula

in which R' is a linear or branched alkyl and/or alkenyl radical having 6 to 22 carbon atoms and Y is an alkali and/or alkaline earth metal, ammonium, alkylammonium, alkanolammonium or glucammonium. If the number is zero (=0), the substance is fatty alcohol sulfate. Preference is given to fatty alcohol ether sulfates (number from 1 to 10). Typical examples are the sulfates of addition products of an average of 1 to 10 and particularly 2 to 5 mol of ethylene oxide to caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, arachidyl alcohol, gadoleyl alcohol, behenyl alcohol, erucyl alcohol and brassidyl alcohol, and technical grade mixtures thereof in the form of their sodium and/or magnesium salts. The ether sulfates may in this connection exhibit both a conventional and a narrowed homolog distribution.

Particular preference is given in the context of the invention to wax dispersions comprising, as c), lauryl ether sulfate having an average ethoxylation level of 1 or 2.

Preferably, c) is present in the aqueous wax dispersions in an amount of 8% to 15%, preferably 9% to 12%, by weight-based on aqueous dispersion.

A particularly uniform particle distribution is obtained in the wax dispersion when a) and c) are advantageously present in a weight ratio in the a):c) range from 2:1 to 4:1 and especially in the range from 2.5:1 to 3.5:1.

Surprisingly, in spite of the presence of the anionic surfactants, no pearlescence and no rise in the viscosity of the wax dispersions is observed.

As a further obligatory constituent, the aqueous dispersions d) comprise amphoteric surfactants selected from the group formed by betaines.

Suitable betaines are, for example, alkyl betaines, alkylamido betaines, alkyl glycinates, imidazolium betaines and sulfo betaines. Betaines are known surfactants that are prepared predominantly by 20 carboxyalkylation, preferably carboxymethylation, of aminic compounds. The starting materials are preferably condensed with halocarboxylic acids or salts thereof, especially with sodium chloroacetate, forming one mole of salt per mole of betaine. In addition, it is also possible to add on unsaturated carboxylic acids, for example acrylic acid. Examples of suitable betaines are the carboxyalkylation products of secondary and especially tertiary amines, which follow the formula (I)

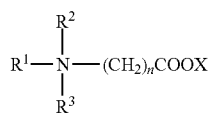

in which $R^1$ represents alkyl and/or alkenyl radicals having 6 to 22 carbon atoms, $R^2$ represents hydrogen or alkyl radicals having 1 to 4 carbon atoms, $R^3$ represents alkyl radicals having 1 to 4 carbon atoms, n represents numbers from 1 to 6 and X represents an alkali metal and/or alkaline earth metal or ammonium.

Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and the technical grade mixtures thereof.

Also additionally suitable are carboxyalkylation products of amido amines that follow the formula (II)

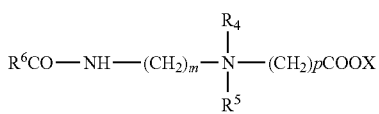

in which $R^6CO$ is an aliphatic acyl radical having 6 to 22 carbon atoms and 0 or 1 to 3 double bonds, m represents numbers from 1 to 3, $R^4$ represents hydrogen or alkyl radicals having 1 to 4 carbon atoms, $R^5$ represents alkyl radicals having 1 to 4 carbon atoms, p represents numbers from 1 to 6 and X represents an alkali metal and/or alkaline earth metal or ammonium.

Typical examples are reaction products of fatty acids $R^6COOH$ having 6 to 22 carbon atoms, namely caproic acid, caprylic acid, capric acid, lauric acid, myristic acid, palmitic acid, palm oleic acid, stearic acid, isostearic acid, oleic acid, elaidic acid, petroselic acid, linoleic acid, linolenic acid, eleostearic acid, arachic acid, gadoleic acid, behenic acid and erucic acid, and the technical grade mixtures thereof, with N,N-dimethylaminoethylamine, N,N-dimethylaminopropylamine, N,N-diethylaminoethylamine and N,N-diethylaminopropylamine, which are condensed with sodium chloroacetate. Preference is given to the use of a condensation product of $C_{8/18}$-coconut fatty acid N,N-dimethylaminopropylamide with sodium chloroacetate.

Also useful as a suitable starting materials for the betaines to be used in the context of the invention are imidazolines that follow the formula (III)

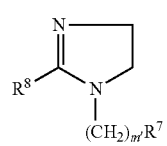

in which $R^7$ is an alkyl radical having 5 to 21 carbon atoms, $R^8$ is a hydroxyl group, an $O-COR^9-$ or $NH-COR^9-$ radical, m' is 2 or 3 and $R^9CO$ is an aliphatic acyl radical having 6 to 22 carbon atoms and 0 or 1 to 3 double bonds. These substances too are known substances which can be obtained, for example, by cyclizing condensation of 1 or 2 mol of fatty acid with polyfunctional amines, for example aminoethylethanolamine (AEEA) or diethylenetriamine. The corresponding carboxyalkylation products are mixtures of different open-chain betaines. Typical examples are condensation products of the fatty acids $R^9COOH$, for example the abovementioned fatty acids $R^6COOH$, with AEEA, preferably imidazolines based on lauric acid or again $C_{12/14}$ coconut fatty acid, which are subsequently betainized with sodium chloroacetate.

A particularly suitable amphoteric surfactant d) is coco (fatty acid amidopropyl)betaine, known by the INCI name Cocamidopropyl Betaine.

The wax dispersions of the invention comprise d) in an amount of 0.5% to 3.0% by weight, preferably 1% to 2.5% by weight—based on aqueous dispersion.

Particularly advantageous wax dispersions are those that comprise c) and d) in a weight ratio of c):d) of 4:1 to 8:1, preferably 5.5:1 to 7.5:1. For instance, wax dispersions with such a weight ratio especially show excellent storage stability.

A preferred aqueous wax dispersion comprises
 a) 25% to 30% by weight of ethylene glycol fatty acid diester, where 85% to 100% by weight of the fatty acid is stearic acid,
 b) 1.0% to 2.0% by weight of glycerol fatty acid monoester, where 90% to 100% by weight of the fatty acid is oleic acid,
 c) 9.0% to 12% by weight of lauryl ether sulfate having an average ethoxylation level of 1 or 2,
 d) 1.0% to 2.5% by weight of coconut fatty acid amidopropyl betaine.

The weight figures here are based on active substance.

In accordance with one embodiment of the present invention, the aqueous wax dispersions of the invention consist of constituents a) to d) and water, and also pH regulators and optionally preservatives.

Examples of suitable preservatives are benzoates, phenoxyethanol, formaldehyde solution, parabens, pentanediol, sorbic acid, levulinic acid and arachidonic acid, and also the silver complexes known under the Surfacine® name, and the additional substance classes listed in Annex 6, parts A and B, of the Cosmetics Directive. Examples of suitable pH regulators are the compatible acids or bases known in the cosmetics industry, which are likewise listed in the Cosmetics Directive.

Particular preference is given to aqueous wax dispersions consisting of
 a) 25% to 30% by weight of ethylene glycol fatty acid diester, where 85% to 100% by weight of the fatty acid is stearic acid,
 b) 1.0% to 2.0% by weight of glycerol fatty acid monoester, where 90% to 100% by weight of the fatty acid is oleic acid,
 c) 9.0% to 12% by weight of lauryl ether sulfate having an average ethoxylation level of 1 or 2, d) 1.0% to 2.5% by weight of coconut fatty acid amidopropyl betaine,
 e) 0.1% to 3.0% by weight of pH regulators,
 f) 0% to 1.5% by weight of preservatives,
 g) water to 100% by weight.

The wax dispersions show low viscosities, preferably below 8000 and especially from 3000 to 6000 mPas (according to Brookfield: 23° C., spindle 5, 10 rpm), good flow and pumping properties, and exceptional fine division of the waxes in the dispersion, recognizable, for example, by the average particle diameter and the particle size distribution.

Without being bound to any theory, what seems to be particularly crucial for the cloudiness characteristics and the conditioning effects is the selection of the wax bodies a) with the particular fatty acid cut in combination with the fatty acid partial glyceride and the selected weight ratio of a):b) thereof. A particularly uniform particle distribution is obtained in the wax dispersion when a) and c) are advantageously present in a weight ratio in the a):c) range from 2:1 to 4:1 and especially in the range from 2.5:1 to 3.5:1.

The present invention therefore further relates to the use of the aqueous wax dispersions of the invention according to any of patent claims 1 to 14 as opacifier in a cosmetic formulation for hair treatment.

The present invention further relates to the use of the wax dispersions of the invention according to any of patent claims 1 to 14 as conditioner, especially for improving wet and dry combability, in a cosmetic formulation for hair treatment.

Cosmetic formulations for hair treatment are understood to mean hair shampoos, hair lotions, hair tonics, hair rinses, hairdrying lotions, hair milk or else formulations for the care of eyebrows and eyelashes.

The wax dispersions of the invention are preferably used in amounts of 1% to 5% by weight—based on cosmetic formulation for hair treatment.

The wax dispersions of the invention cause sustained, homogeneous and, compared to the prior art, particularly intense white cloudiness without generating pearlescence, and, in particular, they also show excellent conditioning effects, such that it is possible if desired to wholly or partly dispense with further conditioning constituents in the cosmetic formulations for haircare.

However, in a further embodiment of the present invention, it is alternatively possible to use the wax dispersions of the invention as a booster for cationic modified polymers with regard to conditioning action.

The invention therefore further relates to the use of the aqueous wax dispersions according to any of claims 1 to 14 as a booster for improving the conditioning action of cationic modified polymers in a cosmetic formulation for hair treatment.

Suitable cationic polymers are, for example, quaternized hydroxyethylcellulose, also obtainable under the UCARE-Polymer® JR 400 name from Amerchol, cationic starch, copolymers of diallylammonium salts and acrylamides, quaternized vinylpyrrolidone/vinylimidazole polymers, for example Luviquat® (BASF), condensation products of polyglycols and amines, quaternized protein hydrolyzates, polypeptides and amino acids, for example lauryldimonium hydroxypropyl hydrolyzed collagen (Lamequat® L/Grunau), quaternized wheat polypeptides, polyethyleneimine, cationic silicone polymers, for example amodimethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides as described, for example, in FR-A 2252840 and also the crosslinked water-soluble polymers thereof, cationic chitin derivatives such as quaternized chitosan, optionally in microcrystalline distribution, condensation products of dihaloalkyls, for example dibromobutane with bisdialkylamines, for example bisdimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol. Especially suitable cationic polymers are polyquaternium-68, obtainable as Luviquat® Supreme AT 1, or polyquaternium-11, obtainable as Luviquat® PQ 11 AT 1.

The wax dispersions boost, i.e. enhance, the conditioning action preferably of cationic polymers selected from the group formed by cationically modified guar, PQ-7 and PQ-10.

Cationically modified guar derivatives such as the quaternized guar derivative Guar Hydroxypropyltrimonium Chloride are commercially available, for example, as Dehyquart® Guar N from BASF Personal Care & Nutrition GmbH. PQ-10, a cationic cellulose derivative, is available under the UCARE® Polymer JR 400 name from Amerchol, and the copolymer of diallylammonium salts and acrylamides known as PQ-7 is commercially available as Dehyquart® CC7 from BASF Personal Care & Nutrition GmbH.

In a further embodiment of the present invention, cosmetic compositions for conditioning hair treatment are claimed, comprising the wax dispersions of the invention, anionic surfactants and cationic polymers, and optionally amphoteric and/or zwitterionic surfactants and emulsifiers or further customary ingredients, and also water for supplementation to 100% by weight.

The following are preferably present in the conditioning hair treatment compositions—based on active substance content:

0.5% to 5.0% by weight, preferably 1.0% to 3% by weight, of wax dispersion of the invention 1.0% to 15% by weight, preferably 7.5% to 12% by weight, of anionic surfactants 0.01% to 1% by weight, preferably 0.05% to 0.4% by weight, of at least one cationically modified polymer and/or 0.0% to 15% by weight, preferably 0.1% to 5% by weight, of amphoteric and/or zwitterionic surfactants, 0.0% to 10% by weight of emulsifiers and optionally further customary ingredients may be present, and water for supplementation to 100% by weight.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, alk(en)ylpolyglycol ether citrates and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, protein fatty acid condensates (especially wheat-based plant products) and alkyl (ether) phosphates. If the anionic surfactants comprise polyglycol ether chains, these may have a conventional homolog distribution, but preferably have a narrowed homolog distribution. The anionic surfactants used are more preferably the fatty alcohol (ether sulfates) that have already been described in association with the wax dispersions of the invention, and especially lauryl ether sulfate with 1 or 2 mol of ethylene oxide.

Typical cationic polymers have already been described above with the use of the wax dispersions as boosters and are preferably selected from the group formed by cationically modified guar, PQ7 and PQ-10. Mixtures of modified guar, PQ-7 and PQ-10 may also be present as cationically modified polymers, preferably mixtures of cationically modified guar and PQ-10, especially in a weight ratio of 1:1.

Suitable amphoteric or zwitterionic surfactants are alkyl betaines, alkylamido betaines, aminopropionates, aminoglycinates, imidazolinium betaines and sulfobetaines. Examples of suitable alkyl betaines are the carboxyalkylation products of secondary and especially tertiary amines. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and also the technical grade mixtures thereof. Also useful, in addition, are carboxyalkylation products of amido amines. Typical examples are reaction products of fatty acids having 6 to 22 carbon atoms, namely caproic acid, caprylic acid, capric acid, lauric acid, myristic acid, palmitic acid, palm oleic acid, stearic acid, isostearic acid, oleic acid, elaidic acid, petroselic acid, linoleic acid, linolenic acid, eleostearic acid, arachic acid, gadoleic acid, behenic acid and erucic acid, and the technical grade mixtures thereof, with N,N-dimethylaminoethylamine, N,N-dimethylaminopropylamine, N,N-diethylaminoethylamine and N,N-diethylaminopropylamine, which are condensed with sodium chloroacetate. Preference is given to the use of a condensation product of $C_{8/18}$-coconut fatty acid-N,N-dimethylaminopropylamide with sodium chloroacetate.

Furthermore, imidazolinium betaines are also included. These substances are also known substances which can be obtained for example by cyclizing condensation of 1 or 2 mol of fatty acid with polyfunctional amines, for example aminoethylethanolamine (AEEA) or diethylenetriamine. The corresponding carboxyalkylation products are mixtures of different open-chain betaines. Typical examples are condensation products of the abovementioned fatty acids with AEEA, preferably imidazolines based on lauric acid or again $C_{12/14}$-coconut fatty acid which are subsequently betainized with sodium chloroacetate.

Emulsifiers

Suitable emulsifiers are, for example, nonionogenic surfactants from at least one of the following groups:
- addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl radical;
- addition products of 1 to 15 mol of ethylene oxide onto castor oil and/or hydrogenated castor oil;
- addition products of 15 to 60 mol of ethylene oxide onto castor oil and/or hydrogenated castor oil;
- adducts having 1 to 30 mol of ethylene oxide onto partial esters of glycerol and/or sorbitan with unsaturated, linear or saturated, branched fatty acids having 12 to 22 carbon atoms and/or hydroxycarboxylic acids having 3 to 18 carbon atoms;
- partial esters of polyglycerol (average degree of self-condensation 2 to 8), polyethylene glycol (molecular weight 400 to 5000), sorbitan, trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof having 1 to 30 mol of ethylene oxide;
- mixed esters of pentaerythritol, fatty acids, citric acid and fatty alcohol and/or mixed esters of fatty acids having 6 to 22 carbon atoms, methylglucose and polyols, preferably glycerol or polyglycerol;
- mono-, di- and trialkyl phosphates, and mono-, di- and/or tri-PEG-alkyl phosphates and salts thereof;
- wool wax alcohols;
- polysiloxane-polyalkyl-polyether copolymers and corresponding derivatives;
- block copolymers, for example polyethyleneglycol-30 dipolyhydroxystearates;
- polymer emulsifiers, for example Pemulen grades (TR-1, TR-2) from Goodrich;
- polyalkylene glycols and
- glycerol carbonate.

Particularly preferred emulsifiers are addition products of ethylene oxide onto $C_{12/18}$-fatty acid mono- and diesters, addition products of 1 to 30, preferably 5 to 10 mol, of ethylene oxide onto hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride, and the technical grade mixtures thereof. Addition products of 1 to 30 mol, preferably 5 to 10 mol, of ethylene oxide onto sorbitan esters are likewise suitable. Useful sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and the technical grade mixtures thereof. Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (IsolanO PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate and mixtures thereof. Examples of further suitable polyol esters are the mono-, di- and triesters of trimethylolpropane optionally reacted with 1 to 30 mol of ethylene oxide or pentaerythritol with lauric acid, coconut fatty acid, tallow fatty acid, palmitic acid, stearic acid, oleic acid, behenic acid and the like. Preference is also given to trimethylpropane EO/PO trioleate, a mixture obtainable by the reaction of trimethylolpropane trioleate with ethylene oxide and propylene oxide under alkaline conditions. Ethylene oxide units (EO) and propylene oxide units (PO) are incorporated, at least in part, into the ester groups of the trimethylolpropane trioleate. The trimethylpropane EO/PO trioleate is characterized by the statistical average of its content of EO and PO units per molecule. In one embodiment of the present invention, trimethylpropane EO/PO trioleate having 120 ethylene oxide units (EO) and 10 propylene oxide units (PO) is used.

Further customary ingredients may be bodying agents, thickeners, superfatting agents, stabilizers, UV stabilizers, biogenic active ingredients and antioxidants, active antidandruff ingredients, film formers, protein hydrolyzates, hydrotropes, preservatives, perfume oils, aromas and colorants.

Suitable consistency regulators are primarily fatty alcohols or hydroxy fatty alcohols having 12 to 22 and preferably 16 to 18 carbon atoms and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are for example Aerosil grades (hydrophilic silicas), polysaccharides, especially xanthan gum, guar gum, agar agar, alginates and tyloses, carboxymethylcellulose, hydroxyethylcellulose and hydroxypropylcellulose, further higher molecular-weight polyethylene glycol monoesters and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Particularly effective substances have also been found to be bentonites, for example Bentone® Gel VS-5PC (Rheox), which is a mixture of cyclopentasiloxane, disteardimonium hectorite and propylene carbonate. Also useful are surfactants, for example ethoxylated fatty acid glycerides, esters of fatty acids with polyols, for example pentaerythritol or trimethylolpropane, fatty alcohol ethoxylates with a narrowed homolog distribution or alkyl oligoglucosides, and electrolytes, such as sodium chloride and ammonium chloride.

Superfatting agents used may be substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers.

Stabilizers used may be metal salts of fatty acids, for example magnesium stearate or ricinoleate, aluminum stearate or ricinoleate and/or zinc stearate or ricinoleate.

UV light protection factors are understood to mean, for example, organic substances (light protection filters) which are liquid or crystalline at room temperature and which are capable of absorbing ultraviolet rays and of re-releasing the energy absorbed in the form of radiation of longer wavelength, for example heat. UVB filters may be oil-soluble or water-soluble. Examples of oil-soluble substances are:

- 3-benzylidenecamphor or 3-benzylidenenorcamphor and derivatives thereof, e.g. 3-(4-methylbenzylidene)camphor described;
- 4-aminobenzoic acid derivatives, preferably 2-ethylhexyl 4-(dimethylamino)benzoate, 2-octyl 4-(dimethylamino)benzoate and amyl 4-(dimethylamino)benzoate;
- esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di-2-ethylhexyl 4-methoxybenzmalonate;
- triazine derivatives, for example 2,4,6-trianilino-(p-carbo-2'-ethyl-1'-hexyloxy)-1,3,5-triazine and Octyl Triazone or Dioctyl Butamido Triazone (Uvasorb® HEB);
- propane-1,3-diones, for example 1-(4-tert-butylphenyl)-3-(4'-methoxyphenyl)propane-1,3-dione;
- ketotricyclo(5.2.1.0)decane derivatives.

Suitable water-soluble substances are:
- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidenecamphor, for example 4-(2-oxo-3-bornylidenemethyl)benzenesulfonic acid and 2-methyl-5-(2-oxo-3-bornylidene)sulfonic acid and salts thereof.

Suitable typical UVA filters are especially derivatives of benzoylmethane, for example 1-(4'-tertbutylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UVA and UVB filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Combinations of this type are advantageously combined with water-soluble filters, for example 2-phenylbenzimidazole-5-sulfonic acid and the alkali metal, alkaline earth metal, ammonium, alkylammonium, alkanolammonium and glucammonium salts thereof.

In addition to the soluble substances mentioned, insoluble light protection pigments, specifically finely dispersed metal oxides and salts, are also useful for this purpose. Examples of suitable metal oxides are especially zinc oxide and titanium dioxide, and additionally oxides of iron, of zirconium, of silicon, of manganese, of aluminum and of cerium, and mixtures thereof. The salts used may be silicates (talc), barium sulfate or zinc stearate. The oxides and salts are used in the form of the pigments for skincare and skin-protecting emulsions and decorative cosmetics. Here, the particles should have an average diameter of less than 100 nm, preferably between 5 and 50 nm and in particular between 15 and 30 nm. They may have a spherical shape, but it is also possible to use those particles which have an ellipsoidal shape or a shape which deviates in some other way from the spherical configuration. The pigments may also be in surface-treated form, i.e. hydrophilized or hydrophobized. Typical examples are coated titanium dioxides, for example titanium dioxide T 805 (Degussa) or Eusolex® T2000 (Merck). Suitable hydrophobic coating agents are in particular silicones and specifically trialkoxyoctylsilanes or simethicones. In sunscreen compositions, preference is given to using so-called micropigments or nanopigments. Preference is given to using micronized zinc oxide.

Biogenic active ingredients are understood to mean, for example, tocopherol, tocopherol acetate, tocopherol palmitate, ascorbic acid, (deoxy)ribonucleic acid and the fragmentation products thereof, β-glucans, retinol, bisabolol, allantoin, phytantriol, panthenol, AHA acids, amino acids, ceramides, pseudoceramides, essential oils, plant extracts, for example *Prunus* extract, bambara nut extract or vitamin complexes.

Antioxidants interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, ylinoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$), selenium and derivatives thereof (e.g. selenomethionine), stilbenes and derivatives thereof (e.g. stilbene oxide, transstilbene oxide) and the derivatives (salts, esters, ethers, sugars, nucleotides, nucleosides, peptides and lipids), suitable in accordance with the invention, of these specified active ingredients.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

Useful active antidandruff ingredients include piroctone olamine (1-hydroxy-4-methyl-6-(2,4,4-trimythylpentyl)-2-(1H)-pyridinonemonoethanolamine salt), Baypival® (climbazole), ketoconazoleo, (4-acetyl-1-{-4-[2-(2,4-dichlorophenyl)-2-(1H-imidazol-1-ylmethyl)-1,3-dioxylan-c-4-ylmethoxyphenyl}piperazine, ketoconazole, Elubiol, selenium disulfide, colloidal sulfur, sulfur polyethylene glycol sorbitan monooleate, sulfur ricinol polyethoxylate, sulfur tar distillates, salicylic acid (and/or in combination with hexachlorophene), undecylenic acid monoethanolamide sulfosuccinate sodium salt, Lamepon® UD (protein-undecylenoic acid condensate), zinc pyrithione, aluminum pyrithione and magnesium pyrithione/dipyrithione-magnesium sulfate.

If desired, protein hydrolyzates known from the prior art may be used, for example based on keratin, such as the commercially available Nutrilan® Keratin W PP, or based on wheat, such as Gluadin® WLM Benz, Gluadin® WK or Gluadin® WP. It is also possible to add small amounts of free amino acids such as lysine or arginine.

Flow behavior may also be improved by using hydrotropes, for example ethanol, isopropyl alcohol or polyols. Polyols which are suitable here preferably have 2 to 15 carbon atoms and at least two hydroxyl groups. The polyols may comprise still other functional groups, in particular amino groups, or be modified with nitrogen. Typical examples are glycerol;
alkylene glycols, for example ethylene glycol, diethylene glycol, propylene glycol, butylene glycol, hexylene glycol, and polyethylene glycols with an average molecular weight of from 100 to 1000 daltons;
technical grade oligoglycerol mixtures with a degree of self-condensation of from 1.5 to 10, for example technical grade diglycerol mixtures with a diglycerol content of 40% to 50% by weight;
methylol compounds, such as especially trimethylolethane, trimethylolpropane, trimethylolbutane, pentaerythritol and dipentaerythritol;
lower alkyl glucosides, especiallythose with 1 to 8 carbon atoms in the alkyl radical, for example methyl and butyl glucoside;
sugar alcohols having 5 to 12 carbon atoms, for example sorbitol or mannitol;
sugars having 5 to 12 carbon atoms, for example glucose or sucrose;
amino sugars, for example glucamine;
dialcoholamines such as diethanolamine or 2-amino-1,3-propanediol.

Examples of suitable preservatives are benzoates, phenoxyethanol, formaldehyde solution, parabens, pentanediol, sorbic acid, levulinic acid and arachidonic acid, and also the silver complexes known under the Surfacine® name, and the additional substance classes listed in Annex 6, parts A and B, of the Cosmetics Directive.

Mention may be made, as perfume oils, of mixtures of natural and synthetic fragrances. Natural fragrances are extracts from flowers (lily, lavender, rose, jasmine, neroli, ylang ylang), stems and leaves (geranium, patchouli, petitgrain), fruits (aniseed, coriander, caraway, juniper), fruit peels (bergamot, lemon, orange), roots (mace, *angelica*, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (*galbanum*, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, aisomethylionone and methyl cedryl ketone, the alcohols include anethole, citronellol, eugenol, isoeugenol, geraniol, linalool, phenylethyl alcohol and terpineol, and the hydrocarbons include primarily the terpenes and balsams. However, preference is given to using mixtures of different fragrances which together produce a pleasant scent note. Essential oils of relatively low volatility, which are mostly used as aroma components, are also suitable as perfume oils, e.g. sage oil, chamomile oil, clove oil, melissa oil, mint oil, cinnamon leaf oil, linden blossom oil,juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, 0-damascone, geranium oil bourbon, cyclohexyl salicylate, vertofix coeur, iso-E-super, Fixolide NP, evernyl, iraldein gamma, phenylacetic acid, geranyl acetate, benzyl acetate, rose oxide, romillate, irotyl and floramate alone or in mixtures. Examples of suitable aromas include peppermint oil, spearmint oil, aniseed oil, star anise oil, caraway oil, *eucalyptus* oil, fennel oil, lemon oil, wintergreen oil, clove oil, menthol and the like.

Dyes which can be used are the substances approved and suitable for cosmetic purposes, as listed, for example, in the publication "Kosmetische Farbemittel" [Cosmetic Colorants] from the Farbstoffkommission der Deutschen Forschungsgemeinschaft [Dyes Commission of the German Research Society], Verlag Chemie, Weinheim, 1984, pp. 81-106. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). As a luminescent dye, it is also possible for luminol to be present. These dyes are usually used in concentrations of from 0.001% to 0.1% by weight, based on the total mixture.

Working Examples of Wax Dispersions:

Inventive wax dispersions A1 to A3 and a wax dispersion for comparison V1 were produced (stated amounts in % by weight of active substance—based on wax dispersion). For this purpose, an initial charge of ⅔ of the total amount of water was heated to 85° C. Ethylene glycol distearate (according to the invention or for comparison), Texapon® N701(=sodium lauryl ether sulfate+1EO), Dehyton® PK45 (=coco(fatty acid amidopropyl)betaine) and Monomuls® (fatty acid partial glyceride) were added to the hot phase and the mixture was stirred. At 64° C., the last ⅓ of the total amount of water was added and the mixture was stirred. After cooling to about 40° C., sodium benzoate, sodium sulfate and citric acid (50% by weight solution) were added and the mixture was stirred.

The wax dispersions of the invention comprise Cutina® KE 2747 as ethylene glycol fatty acid diester; the wax dispersion for comparison V1 comprises Cutina® AGS with the following specification:

Composition of ethylene glycol distearate (diester, monoester and fatty acid with corresponding carbon chain distribution between $C_{16}$ and $C_{18}$ and $C_{18}$:

| | Carbon chain distribution $C_{16}$ and $C_{18}$ | | GC wt % | |
|---|---|---|---|---|
| | % $C_{16}$ + $C_{20}$ + $C_{22}$ | % $C_{18}$ | Monoester | Diester |
| Invention Cutina ® KE 2747 | 2-10 | 90-98 | 6 | 94 |
| Comparison Cutina ® AGS | 48-52 | 48-52 | 8 | 92 |

The composition and the properties of the wax dispersions can be found in table 1.

Wax dispersion V2, by contrast with the wax dispersions of the invention, does not comprise any betaine, but instead comprises the nonionic surfactant lauryl glucoside according to DE 1951572C.

TABLE 1

Wax dispersions (figures in % by weight of active substance-based on the final composition)

| Composition (INCI) | A1 | A2 | A3 | V1 | V2 |
|---|---|---|---|---|---|
| Wax body (a) Cutina ® KE 2747 Ethylene glycol distearate | 27 | 27 | 27 | — | 27 |
| Wax body (a) Cutina ® AGS Ethylene glycol distearate | — | — | — | 27 | — |
| Monomuls ® 90-O18 (b) Glyceryl oleate | 1.55 | — | — | 1.55 | — |
| Monomuls ® 90-L12 (b) Glyceryl laurate | — | — | 1.55 | — | 1.55 |
| Monomuls ® 60-35C (b) Glyceryl stearate | — | 1.55 | — | — | — |
| Sodium lauryl ether sulfate 1 EO (c) | 10.15 | 10.15 | 10.15 | 10.15 | 10.15 |
| Plantacare ® 1200UP Lauryl glucoside | — | — | — | — | 15.5 |
| Cocoamidopropyl betaine (d) | 1.73 | 1.73 | 1.73 | 1.73 | — |
| Na benzoate | 0.5 | 0.5 | 0.5 | 0.5 | 0.5 |
| Citric acid 50% | 0.6 | 0.6 | 0.6 | 0.6 | — |
| Water | Ad100 | Ad100 | Ad100 | Ad100 | Ad 100 |
| pH | 4.7 | 4.7 | 4.7 | 4.7 | 4.7 |
| Weight ratio a:b | 17.4:1 | 17.4:1 | 17.4:1 | 17.4:1 | 17.4:1 |
| Weight ratio c:d | 6.5:1 | 6.5:1 | 6.5:1 | 6.5:1 | — |
| Weight ratio a:c | 2.7:1 | 2.7:1 | 2.7:1 | 2.7:1 | 2.7:1 |

TABLE 1-continued

Wax dispersions (figures in % by weight of active substance-based on the final composition)

| Composition (INCI) | A1 | A2 | A3 | V1 | V2 |
|---|---|---|---|---|---|
| Viscosity in mPas | 5500 | 8000 | 7200 | 15 500 | 35 000 |
| Particle size d50 in µm | 1 | 2 | 1.7 | 5 | 11 |
| Particle size d90 in µm | 3.5 | 6 | 5 | 12 | 19 |
| Average particle diameter | 1.3 | 2.4 | 2 | 8.5 | 12 |
| Appearance | cloudy | cloudy | cloudy | pearlescent | pearlescent |

Fine division was determined via determination of the particle size distribution in µm and the average particle diameter in µm by means of laser diffraction (Mastersizer 2000) (see product description from MALVERN INSTRUMENTS GmbH, Marie-Curie-Straße 4/1, 71083 Herrenberg, Germany). Viscosity was ascertained by the Brookfield method (23° C., spindle 5, 10 rpm, mPas).

It is apparent from table 1 that wax dispersions comprising ethylene glycol fatty acid diester having a C18 content of at least 90% (A1 to A3) are an opacifier. Wax dispersion A1 is of particularly low viscosity and has a small particle size. Wax dispersions comprising an ethylene glycol fatty acid diester with a small C18 content show pearlescence, higher viscosity and greater particle diameter (see V1). Wax dispersions comprising lauryl glucoside in place of betaine as surfactant according to DE 19511572C also have pearlescence, higher viscosity and greater particle sizes (see V2).

B) Use of the Wax Dispersions in Hair Shampoo Formulations:

Mixing the following constituents at 25° C. produced aqueous white hair shampoo formulations with the following conditioner performances:

TABLE 2

Amount (% by weight) as is

| Formulations | B1 | B2 | B3 | B4 (=comparison) | B5 (=comparison) | B6 (=comparison) |
|---|---|---|---|---|---|---|
| Wax dispersion according to A1) | 2.20 | 2.20 | 2.20 | — | — | — |
| Dehyton PK ® 45 (INCI Cocoamidopropyl betaine; 45%) | 5.40 | 5.40 | 5.40 | 5.40 | 5.40 | 5.40 |
| Texapon ® N70 (INCI: Sodium Laureth Sulfate + 2EO 70%) | 14.30 | 14.30 | 14.30 | 14.30 | 14.30 | 14.30 |
| Dehyquart ® Guar N (INCI: Guar Hydroxypropyltrimonium Chloride; | 0.20 | 0.10 | | | | |
| UCARE Polymer ® JR 400 (=INCI: Polyquaternium-10; | | 0.10 | | | | 0.20 |
| Euperlan ® PCO (=INCI: Styrene/Acrylates Copolymer (and) Coco-Glucoside; 40%) | | | | | 1.00 | |
| Glycerol (99.5%) | 1.50 | 1.50 | 1.50 | 1.00 | 1.00 | 1.00 |
| Perfume "Cotton Touch" | 0.50 | 0.50 | 0.50 | 0.50 | 0.50 | 0.50 |
| Sodium Benzoate | 0.50 | 0.50 | 0.50 | 0.50 | 0.50 | 0.50 |
| Citric acid (50%) | 0.65 | 0.65 | 0.61 | 0.73 | 0.62 | 0.66 |
| Sodium chloride | 1.15 | 1.23 | 1.39 | 1.07 | 1.29 | 1.41 |
| Water | 73.60 | 73.52 | 73.60 | 76.30 | 75.19 | 76.03 |
| Wet combability | 56 (+−8) | 50 (+−6) | 56 (+−7) | 83 (+−8) | 93 (+−11) | 80 (+−11) |
| Dry combability | 30 (+−3) | 27 (+−2) | 44 (+−10) | 68 (+−11) | 180 (+−43) | 124 (+−4) |
| Whiteness (School grades 1-6) | 1+ | 1 | 1 | transparent | 1 | transparent |

UCARE Polymer® JR 400 is what is called a Polyquaternium-10 (=PQ-10); Dehyquart® Guar N is a cationically modified Guar Hydroxypropyltrimonium Chloride; both are cationic polymers.

School grades were awarded for the assessment of whiteness by comparison with B5, which was set as standard.

Residual wet combability/residual dry combability was determined as follows:

Pretreatment of hair tresses:

Residual wet combability: The hair tresses (Caucasian hair, 12 cm/1 g, International Hair Importers & Products, USA) were washed with 6% sodium lauryl ether sulfate solution (active substance content), pH 6.5, and bleached with a solution of 5% hydrogen peroxide at pH 9.4 for 20 minutes, followed by an intensive rinse of the hair.

Residual dry combability: The hair tresses (Caucasian hair, 15 cm/2 g, International Hair Importers & Products, USA) were washed with 6% sodium lauryl ether sulfate solution (active substance content), pH 6.5, and bleached with a solution of 8.5% hydrogen peroxide at pH 9.4 for 20 minutes, followed by two rinses of the hair. This was followed by drying in a stream of air at max. 55° C. for 30 min.

Treatment of the hair tresses with formulations B1) to B6)

In an automated method, a blank measurement was first effected, and then a measurement after the treatment of the hair with the inventive formulations B1) to B3) and, for comparison, with B4) to B6). For this purpose, the hair was treated with 0.25 g/g of hair for 5 min.

In the automated system of the wet combing apparatus, the treated hair tresses were rinsed under standard conditions (38° C., 1 l/minute) for 1 minute and measured.

For the determination of dry combability, the treated hair tresses were stored at 30° C. and 40% relative air humidity for 16 hours.

For each determination, 10 hair tresses were tested and the combing forces were measured over 23 comb movements (3rd to 23rd).

% residual combability was calculated as follows:

Residual combability (%)=(residual combing work after product treatment:combing work before product treatment)×100.

It becomes clear from table B) that the hair shampoo formulations B1+B2+B3 comprising the wax dispersions according to A1) show better residual wet and dry combability than formulations without wax dispersions. This is also true when cationic polymers are present in the hair shampoo formulations (see B1 is better compared to B4). With regard to residual wet and dry combability, hair shampoo formulations B1) and B2) that additionally comprise cationically modified polymers as well as the wax dispersion A1) are particularly good. Accordingly, the wax dispersion itself behaves as a conditioner (see B3) and is also a booster for cationically modified polymers.

The invention claimed is:

1. An aqueous wax dispersion suitable as opacifier and/or conditioner for cosmetic formulations, comprising
    a) 20% to 35% by weight, based on the aqueous dispersion, of an ethylene glycol fatty acid ester as wax body and
    b) 0.5% to 3.0% by weight, based on the aqueous dispersion, of a fatty acid partial glyceride and
    c) 8% to 15% by weight, based on the aqueous dispersion, of an anionic surfactant selected from the group formed by fatty alcohol ether sulfates and
    d) an amphoteric surfactant selected from the group formed by betaines,
    wherein the ethylene glycol fatty acid ester (a) is formed by stearic acid or a mixture of fatty acids comprising 85-100% by weight, based on fatty acid, of stearic acid;
    wherein the average particle diameter of (a) is in the range from 1 to 4 µm; and
    wherein the wax dispersion does not result in pearlescence.

2. The aqueous wax dispersion according to claim 1, wherein the ethylene glycol fatty acid ester present as a) is formed from 90% to 98% by weight of stearic acid and 2% to 10% by weight of other saturated fatty acids having 16 to 22 carbon atoms, based on the total amount of fatty acid.

3. The aqueous wax dispersion according to claim 1, wherein the fatty acid partial glyceride (b) is selected from the group formed by glycerol fatty acid monoesters, wherein the fatty acids have 12 to 18 carbon atoms.

4. The aqueous wax dispersion according to claim 1, wherein a) and b) are present in the dispersion in a weight ratio of a):b)=15:1 to 20:1.

5. The aqueous wax dispersion according to claim 1, wherein c) is selected from the group formed by lauryl ether sulfate having an average ethoxylation level of 1 to 2.

6. The aqueous wax dispersion according to claim 1, wherein a) and c) are present in the dispersion in a weight ratio of a):c)=2:1 to 4:1.

7. The aqueous wax dispersion according to claim 1, wherein d) is selected from the group formed by coco fatty acid amidopropyl betaine.

8. The aqueous wax dispersion according to claim 1, wherein d) is present in an amount of 0.5% to 3.0%, by weight, based on the aqueous dispersion.

9. The aqueous wax dispersion according to claim 1, wherein c) and d) are present in the dispersion in a weight ratio of c):d)=4:1 to 8:1.

10. The aqueous wax dispersion according to claim 1, which comprises a) to d), water, pH regulators, and optionally a preservative.

11. A method of opacifying a cosmetic formulation for hair treatment comprising the use of the aqueous wax dispersion according to claim 1.

12. A method of conditioning the hair comprising the use of the aqueous wax dispersion according to claim 1 in a cosmetic formulation for hair treatment.

13. A method of improving the conditioning action of a cationic modified polymer in a cosmetic formulation for hair treatment comprising the use of the aqueous wax dispersion according to claim 1, in an amount of 1% to 5%, by weight, based on the formulation for hair treatment.

14. The method according to claim 13, wherein the cationically modified polymer is selected from the group formed by cationically modified guar, PQ-7, and PQ-10.

15. A cosmetic composition for conditioning hair treatments comprising the aqueous wax dispersion according to claim 1 and anionic surfactants and cationic polymers, and optionally amphoteric/zwitterionic surfactants, emulsifiers or further customary ingredients, and water for supplementation to 100% by weight.

16. The aqueous dispersion according to claim 3, where the fatty acid partial glyceride (b) is a glycerol fatty monoester of a fatty acid mixture comprising 90% to 100% by weight oleic acid, based on the fatty acid mixture.

17. An aqueous wax dispersion suitable as opacifier and/or conditioner for cosmetic formulations, comprising
  a) 20% to 35% by weight, based on the aqueous dispersion, of an ethylene glycol fatty acid ester as wax body and
  b) 0.5% to 3.0% by weight, based on the aqueous dispersion, of a fatty acid partial glyceride and
  c) 8% to 15% by weight, based on the aqueous dispersion, of an anionic surfactant selected from the group formed by fatty alcohol ether sulfates and
  d) an amphoteric surfactant selected from the group formed by betaines,
  wherein the ethylene glycol fatty acid ester (a) is formed by stearic acid or a mixture of fatty acids comprising 85-100% by weight, based on fatty acid, of stearic acid;
  wherein the average particle diameter of (a) is in the range from 1 to 4 µm;
  wherein the wax dispersion does not result in pearlescence; and
  wherein the wax dispersion has a viscosity below 8000 mPas according to Brookfield: 23° C., spindle 5, 10 rpm.

18. An aqueous wax dispersion suitable as opacifier and/or conditioner for cosmetic formulations, comprising
  a) 20% to 35% by weight, based on the aqueous dispersion, of an ethylene glycol fatty acid ester as wax body and
  b) 0.5% to 3.0% by weight, based on the aqueous dispersion, of a fatty acid partial glyceride and
  c) 8% to 15% by weight, based on the aqueous dispersion, of an anionic surfactant selected from the group formed by fatty alcohol ether sulfates and
  d) an amphoteric surfactant selected from the group formed by betaines,
  wherein the ethylene glycol fatty acid ester (a) is formed by stearic acid or a mixture of fatty acids comprising 85-100% by weight, based on fatty acid, of stearic acid;
  wherein the average particle diameter of (a) is in the range from 1 to 4 µm;
  wherein the wax dispersion does not result in pearlescence; and
  wherein the wax dispersion has a viscosity from 3000 to 6000 mPas according to Brookfield: 23° C., spindle 5, 10 rpm).

* * * * *